(12) United States Patent
Tsuyuki et al.

(10) Patent No.: US 8,351,565 B2
(45) Date of Patent: Jan. 8, 2013

(54) X-RAY CT APPARATUS

(75) Inventors: Masaharu Tsuyuki, Nasushiobara (JP); Miwa Okumura, Utsunomiya (JP); Yasuko Fujisawa, Otawara (JP)

(73) Assignees: Kabushiki Kaisha Toshiba, Tokyo (JP); Toshiba Medical Systems Corporation, Otawara-shi (JP)

( * ) Notice: Subject to any disclaimer, the term of this patent is extended or adjusted under 35 U.S.C. 154(b) by 0 days.

(21) Appl. No.: 12/177,262

(22) Filed: Jul. 22, 2008

(65) Prior Publication Data

US 2009/0028289 A1 Jan. 29, 2009

(30) Foreign Application Priority Data

Jul. 24, 2007 (JP) ................................ 2007-191922

(51) Int. Cl.
*G01N 23/00* (2006.01)
(52) U.S. Cl. ................................. 378/8; 378/4
(58) Field of Classification Search .................. 378/4–20
See application file for complete search history.

(56) References Cited

U.S. PATENT DOCUMENTS

| 6,188,744 | B1 * | 2/2001 | Shinohara et al. ................. 378/8 |
| 7,054,406 | B2 | 5/2006 | Ikeda et al. |
| 2003/0161435 | A1 * | 8/2003 | Ozaki ............................... 378/4 |
| 2005/0249329 | A1 * | 11/2005 | Kazama et al. ................. 378/16 |
| 2007/0237286 | A1 * | 10/2007 | Imai ................................. 378/4 |
| 2008/0107233 | A1 * | 5/2008 | Sakaguchi et al. .............. 378/91 |

FOREIGN PATENT DOCUMENTS

| JP | 2003-319934 | 11/2003 |
| JP | 2004-113779 | 4/2004 |

OTHER PUBLICATIONS

Japanese Office Action mailed on Apr. 3, 2012, issued for JP Application No. 2007-191922, (with English translation).

* cited by examiner

*Primary Examiner* — Hoon Song
(74) *Attorney, Agent, or Firm* — Oblon, Spivak, McClelland, Maier & Neustadt, L.L.P.

(57) ABSTRACT

A CT value of an image within a region of interest is calculated with time. While the calculated CT value does not exceed a predetermined threshold value, a reconstruction mode used when an image is reconstructed from projection data is set to half reconstruction. On the other hand, while the calculated CT value exceeds a predetermined threshold value, the reconstruction mode is set to segment reconstruction.

11 Claims, 9 Drawing Sheets

X-RAY CT APPARATUS

CROSS-REFERENCE TO RELATED APPLICATIONS

This application is based upon and claims the benefit of priority from the prior Japanese Patent Application No. 2007-191922, filed on Jul. 24, 2007; the entire contents of which are incorporated herein by reference.

BACKGROUND OF THE INVENTION

1. Field of the Invention

The present invention relates to an X-ray computed tomography (CT) apparatus that irradiates a subject with X-rays, collects projection data, and reconstructs an image from the collected projection data. In particular, the present invention relates to electrocardiographic synchronized imaging in which imaging is performed synchronously with a cardiac cycle of a heart.

2. Description of the Related Art

Conventionally, an X-ray CT apparatus irradiates a subject with X-rays and collects projection data by detecting the X-rays passing through the subject. The X-ray CT apparatus then reconstructs an image from the collected projection data. In an examination performed using the X-ray CT apparatus, a contrast medium is often used to pick up a clear image of organs and blood vessels to be imaged. However, blood flow causes the contrast medium to flow out from the organs and blood vessels with time. Therefore, when the contrast medium is used, a timing at which to irradiate an imaging subject with the X-rays becomes important.

A technology is disclosed (refer to, for example, JP-A 2004-113779 (KOKAI)) in which a CT value of a region of interest set in consecutively obtained images is successively measured, and imaging conditions (such as a tube current, a timing at which to start imaging, and a timing at which to complete imaging) are controlled based on changes with time in the measured CT value.

In recent years, heart examinations have generally been performed using the X-ray CT apparatus. When the X-ray CT apparatus is used to image a heart, the contrast medium is used and electrocardiographic synchronized imaging is performed. In electrocardiographic synchronized imaging, imaging is performed synchronously with a cardiac cycle of the heart. An electrocardiograph detects the cardiac cycle of the heart. Projection data of a specific phase range is collected at each detected cardiac cycle. To suppress radiation exposure of a subject, the X-rays are intermittently irradiated at each cardiac cycle.

Various types of heart examinations using the X-ray CT apparatus are performed depending on a purpose of examination and a region to be examined. For example, a myocardial perfusion is performed to examine myocardial blood flow. A CT angiography (CTA) is performed to check for coronary artery stenosis and the like. A cardiac function analysis (CFA) is performed to examine a function of an entire heart (heart function).

As stated above, a plurality of types of heart examinations using the X-ray CT apparatus are performed, each type having a different purpose of examination and involving a different region to be examined. Therefore, an X-ray exposure timing, a phase range of projection data required when reconstructing an image, and a temporal resolution of an image obtained through an examination differ with each examination type.

Here, the temporal resolution refers to a temporal element included in the image. As a result of improvement (shortening) in the temporal resolution when reconstructing the image from the projection data, an image that is little affected by movement can be obtained. Reconstruction methods that improve the temporal resolution are, for example, half reconstruction and segment reconstruction.

In a half reconstruction operation, the image is reconstructed using projection data collected while an X-ray tube is rotating within a range of 180 degrees plus $\alpha$ ($\alpha$ being a fan angle). Compared to when the image is reconstructed using 360-degree range projection data (full reconstruction), the half reconstruction can shorten the temporal resolution by approximately one-half.

On the other hand, in a segment reconstruction operation, pieces of projection data of a same cross-section and a same phase are extracted from pieces of projection data of a predetermined number of heartbeats. The extracted pieces of projection data are combined to form a piece of projection data of a range of 180 degrees plus $\alpha$. Subsequently, the half reconstruction operation is performed. Compared to when the image is reconstructed using the 360 degree range projection data, the segment reconstruction can shorten the temporal resolution to about $(180+\alpha)/n$ when an n number of heartbeats are used. The segment reconstruction can further improve temporal resolution, compared to the half reconstruction. A set of pieces of projection data used in a single segment reconstruction operation is referred to, hereinafter, as a projection data set.

By considering an optimal X-ray exposure timing, a projection data phase range, and a temporal resolution for each examination, for example, in the myocardial perfusion, the myocardial blood flow may be confirmed as a purpose of examination to be checked. The region to be examined is a cardiac muscle. Therefore, the X-ray exposure timing is not particularly limited. The projection data is merely required to be of a specific phase range. Compared to blood vessels and the like, the cardiac muscle is an organ having a large structure. Therefore, the temporal resolution is not required to be high.

In the CTA, the purpose of examination is to check for coronary artery stenosis and the like. The region to be examined is blood vessels. Therefore, the X-ray exposure timing is preferably when a concentration of the contrast medium is as high as possible. The projection data is merely required to be of a specific phase range. Because the blood vessels are extremely narrow organs, a high temporal resolution is required.

In CFA, the purpose of examination is to examine heart function. The region to be examined is the entire heart. Therefore, the X-ray exposure timing is preferably when the concentration of the contrast medium is as high as possible. The projection data of all phase ranges in a cardiac cycle is required. Because the entire heart is a large organ, the temporal resolution is not required to be high.

Here, the concentration of the contrast represents the extent of contrast enhancement.

In this way, the X-ray exposure timing required when taking the image obtained through the examination, and the projection data phase range and the temporal resolution required when reconstructing the image differ from each examination type. Therefore, imaging is ordinarily performed at each examination in accordance with a type of the examination.

However, in actuality, a plurality of the examinations described above are often collectively performed during a series of electrocardiographic synchronized imaging operations in consideration of a burden of a patient that is the subject. In this case, during the series of electrocardiographic synchronized imaging operations, based on the examination type, an operator is required to measure an optimal timing while checking the concentration of the contrast medium and, at the same time, irradiate the heart with X-rays in the required phase range. The operator is also required to operate the X-ray CT apparatus to reconstruct the image from the projection data using the required reconstruction mode. Although the operation is conventionally performed manually, the operation is very complicated.

Therefore, when the examinations are collectively performed in during the series of electrocardiographic synchronized imaging operations, how to efficiently collect the projection data required in each examination and reconstruct the required image while suppressing the radiation exposure of the subject is an important issue.

SUMMARY OF THE INVENTION

According to one aspect of the present invention, an X-ray CT apparatus includes an electrocardiographic information collecting unit that collects electrocardiographic information; a data collecting unit that collects projection data obtained by irradiating a subject with X-rays; an image reconstructing unit that reconstructs an image based on the electrocardiographic information collected by the electrocardiographic information collecting unit and the projection data collected by the data collecting unit; a concentration calculating unit that determines a concentration of a contrast medium with time within a region of interest; and a reconstruction condition changing unit that changes reconstruction conditions related to reconstruction of the image based on the concentration determined by the concentration calculating unit.

According to another aspect of the present invention, an X-ray CT apparatus includes an electrocardiographic information collecting unit that collects electrocardiographic information; a data collecting unit that collects projection data obtained by irradiating a subject with X-rays; an image reconstructing unit that reconstructs an image based on the electrocardiographic information collected by the electrocardiographic information collecting unit and the projection data collected by the data collecting unit; a concentration calculating unit that determines a concentration of a contrast medium with time within a region of interest; and an X-ray controlling unit that switches between synchronizing an exposure dose of the X-rays with the electrocardiographic information and asynchronizing the exposure dose of the X-rays with the electrocardiographic information, based on the concentration determined by the concentration calculating unit.

According to still another aspect of the present invention, an X-ray CT apparatus includes an electrocardiographic information collecting unit that collects electrocardiographic information; a data collecting unit that collects projection data obtained by irradiating a subject with X-rays; an image reconstructing unit that reconstructs an image based on the electrocardiographic information collected by the electrocardiographic information collecting unit and the projection data collected by the data collecting unit; a concentration calculating unit that chronologically determines a concentration of a contrast medium with time within a region of interest; a reconstruction condition changing unit that changes reconstruction conditions related to reconstruction of the image based on the concentration determined by the concentration calculating unit; a display unit that displays information indicating changes in the concentration of the contrast medium with time determined by the concentration calculating unit and an interface for receiving an instruction to change imaging conditions related to irradiation of the X-rays; a changing instruction input unit that receives an instruction to change imaging conditions through the interface displayed by the display unit; and an imaging condition changing unit that changes the imaging conditions related to irradiation of the X-rays when the instruction to change the imaging conditions is received by the changing instruction input unit.

DETAILED DESCRIPTION OF THE INVENTION

Exemplary embodiments of the present invention are below described with reference to the attached drawings. An X-ray CT apparatus described herein can take an image of various regions on a subject in the same manner as a common X-ray CT apparatus. However, when the X-ray CT apparatus performs electrocardiographic synchronized imaging using a contrast medium will mainly be described. The X-ray CT apparatus is described under an assumption that at least two or more examinations, among a myocardial perfusion, a CTA, and a CFA, are collectively performed during a series of electrocardiographic synchronized imaging operations.

Figure 1:
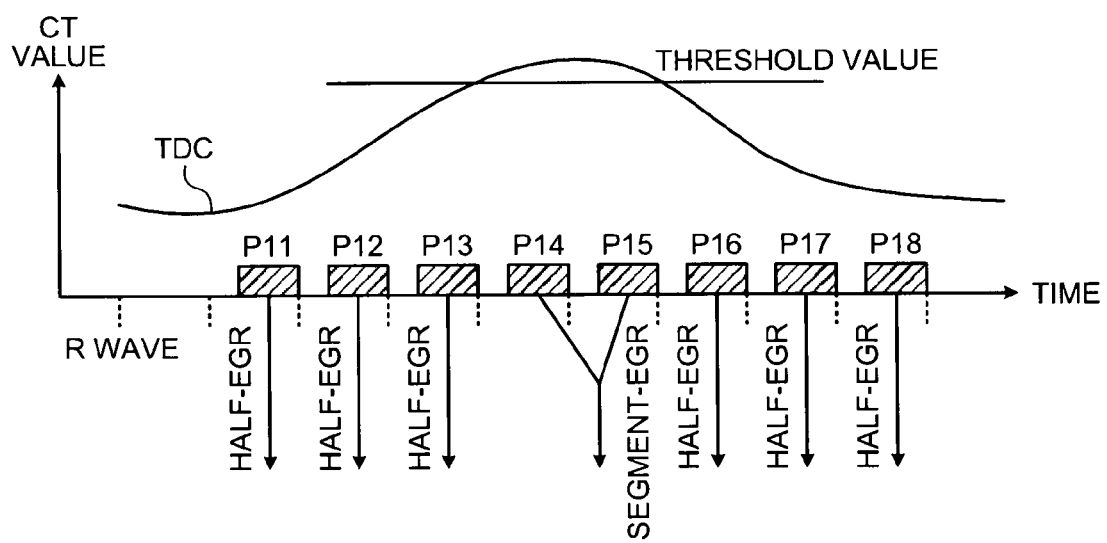
FIG. 1 is an explanatory diagram explaining a concept of electrocardiographic synchronized imaging performed by an X-ray CT apparatus according to a first embodiment.

First, a concept of electrocardiographic synchronized imaging performed by an X-ray CT apparatus according to a first embodiment will be described. FIG. 1 is an explanatory diagram explaining the concept of electrocardiographic synchronized imaging performed by the X-ray CT apparatus according to the first embodiment. Changes in a CT value with time in an image reconstructed after the contrast medium is injected and X-ray exposure timings are shown in FIG. 1. A time density curve (TDC) is a curved line indicating the changes with time in the CT value. "P11" to "P18" respectively indicate the X-ray exposure timings, the horizontal width indicates an X-ray exposure duration, and the height indicates an X-ray exposure strength.

The X-ray CT apparatus according to the first embodiment detects a cardiac cycle of a subject's heart based on an electrocardiographic signal ("R wave" in FIG. 1) outputted from an electrocardiograph. The X-ray CT apparatus irradiates the heart with X-rays of a specific phase range at each detected cardiac cycle and collects projection data. The X-ray CT apparatus then reconstructs an image from the collected projection data.

The X-ray CT apparatus calculates the CT value of the image with time within a region of interest, the CT value serving as an indicator of a concentration of the contrast medium injected into the heart. Based on the calculated CT value, the X-ray CT apparatus changes a reconstruction mode used when the image is reconstructed from the projection data.

Here, the concentration of the contrast represents the extent of contrast enhancement.

Specifically, the X-ray CT apparatus calculates the CT value of the image within the region of interest that is set in advance. When the calculated CT value does not exceed a predetermined threshold value, the X-ray CT apparatus uses half reconstruction ("HALF-EGR" in FIG. 1) as the reconstruction mode used when the image is reconstructed from the projection data. On the other hand, when the calculated CT value exceeds a predetermined threshold value, the X-ray CT apparatus uses segment reconstruction ("SEGMENT-EGR" in FIG. 1) as the reconstruction mode.

In other words, at a timing at which the region of interest has a low concentration of the contrast medium, the X-ray CT apparatus according to the first embodiment collects the projection data of a specific phase range and reconstructs the image from the collected projection data using half reconstruction. The image is suitable for the myocardial perfusion. In the myocardial perfusion, an X-ray exposure timing is not particularly limited, the projection data is merely required to be of the specific phase range, and temporal resolution is not required to be high.

On the other hand, at a timing at which the region of interest has a high concentration of the contrast medium, the X-ray CT apparatus collects the projection data of a specific phase range and reconstructs the image from the collected projection data using segment reconstruction. The image is suitable for the CTA. In the CTA, the X-rays are required to be irradiated at the timing at which the concentration of the contrast medium is as high as possible, the projection data is merely required to be of the specific phase range, and a high temporal resolution is required.

Based on characteristics such as those above, in the X-ray CT apparatus according to the first embodiment, when the examinations (myocardial perfusion and CTA) are collectively performed during the series of electrocardiographic synchronized imaging operations, the projection data required for each examination can be efficiently collected and the required image can be reconstructed while suppressing radiation exposure of the subject.

Figure 2:
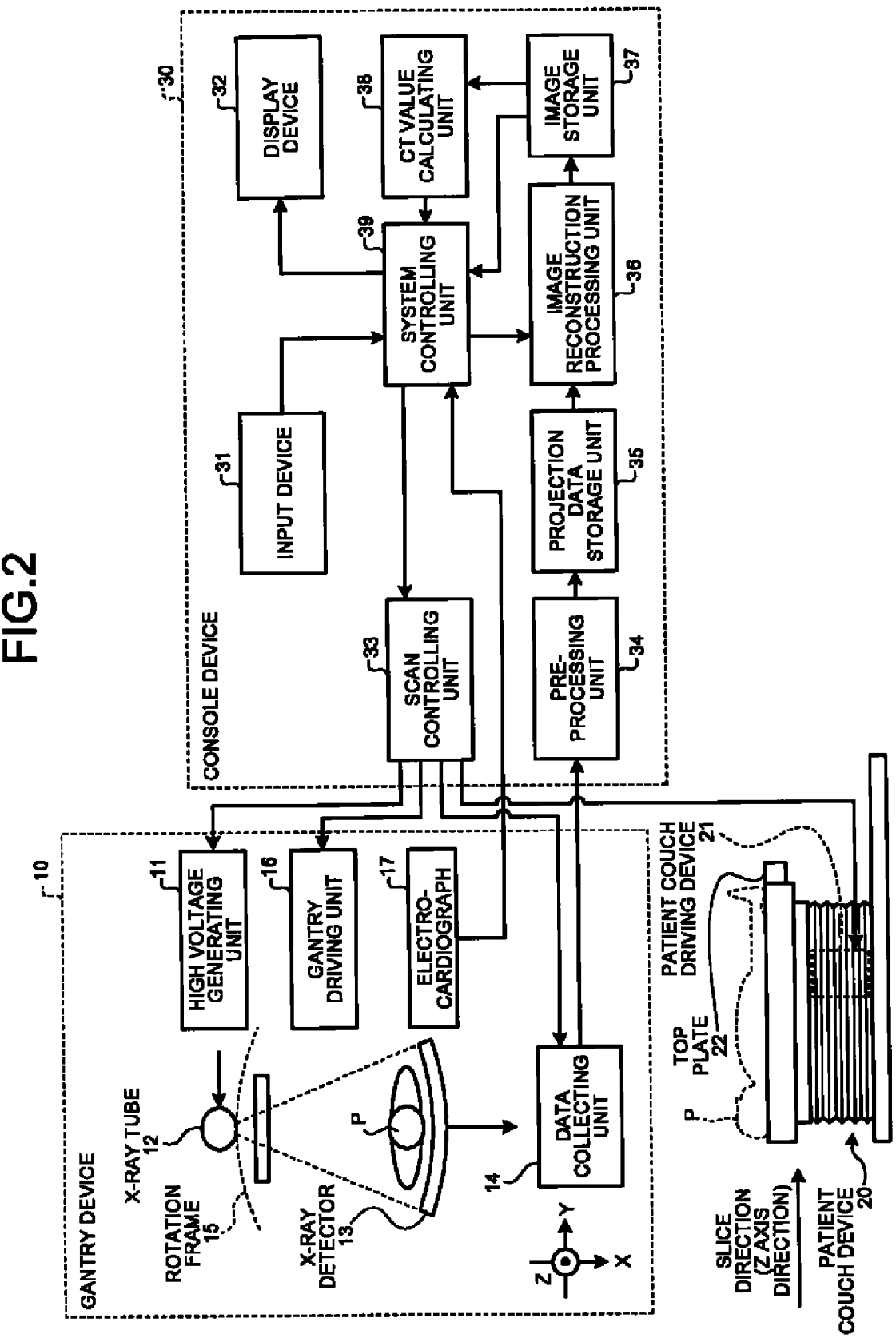
FIG. 2 is a functional block diagram of a configuration of the X-ray CT apparatus according to the first embodiment.

Next, a configuration of the X-ray CT apparatus according to the first embodiment will be described. FIG. 2 is a functional block diagram of a configuration of the X-ray CT apparatus according to the first embodiment. The X-ray CT apparatus includes a gantry device 10, a patient couch device 20, and a console device 30.

The gantry device 10 irradiates a subject P with X-rays and collects projection data. The gantry device 10 includes a high voltage generating unit 11, an X-ray tube 12, an X-ray detector 13, a data collecting unit 14, a rotation frame 15, a gantry driving unit 16, and an electrocardiograph 17.

The high voltage generating unit 11 supplies the X-ray tube 12 with a high voltage. The X-ray tube 12 is a vacuum tube that generates the X-rays using the high voltage supplied from the high voltage generating unit 11. The X-ray detector 13 detects the X-rays passing through the subject P. The data collecting unit 14 generates the projection data using the X-rays detected by the X-ray detector 13.

The rotation frame 15 is a ring-shaped frame continuously rotating at a high speed. The rotation frame 15 holds the X-ray tube 12 and the X-ray detector 13 so that the X-ray tube 12 and the X-ray detector 13 face each other with the subject P therebetween. The gantry driving unit 16 rotatably drives the rotation frame 15, thereby revolving the X-ray tube 12 and the X-ray detector 13 on a circular orbit centering on the subject P. The electrocardiograph 17 detects a weak current generated from the subject P's heart by an electrode attached to the subject P. The electrocardiograph 17 then outputs an electrocardiographic signal based on the detected current.

The subject P is placed on the patient couch device 20. The patient couch device 20 includes a top plate 22 and a patient couch driving device 21. The subject P is placed on the top plate 22 when imaging is performed. The patient couch driving device 21 moves the top plate 22 in a slice direction.

The console device 30 receives operation input to drive the X-ray CT apparatus operated by an operator. The console device 30 also reconstructs an image from the projection data collected by the gantry device 10. The console device 30 includes an input device 31, a display device 32, a scan controlling unit 33, a pre-processing unit 34, an projection data storage unit 35, an image reconstruction processing unit 36, an image storage unit 37, a CT value calculating unit 38, and a system controlling unit 39.

The input device 31 is a mouse, a keyboard, and the like used by the operator to enter instructions for the X-ray CT apparatus. The display device 32 displays an image stored in the image storage unit 37 described hereinafter and the like. The scan controlling unit 33 is a processing unit that irradiates the subject P's heart with the X-rays and collects the projection data by driving the high voltage generating unit 11, the data collecting unit 14, the gantry driving unit 16, and the patient couch driving device 21 based on imaging conditions specified by the system controlling unit 39, under control of the system controlling unit 39 described hereinafter.

The pre-processing unit 34 is a processing unit that performs pre-processing, such as sensitivity correction, of the projection data generated by the data collecting unit 14. The projection data storage unit 35 stores the projection data pre-processed by the pre-processing unit 34.

The image reconstruction processing unit 36 reconstructs the image from the projection data stored in the projection data storage unit 35 based on the reconstruction conditions specified by the system controlling unit 39, under control of the system controlling unit 39. The image reconstruction processing unit 36 provides a function for reconstructing the image using at least half reconstruction and segment reconstruction. The image reconstruction processing unit 36 changes a reconstruction mode between the half reconstruction and the segment reconstruction, based on the reconstruction conditions specified by the system controlling unit 39. A number of heartbeats used when the image is reconstructed using segment reconstruction is set in advance by the operator.

The image storage unit 37 stores the image reconstructed by the image reconstruction processing unit 36. The CT value calculating unit 38 calculates the CT value of the region of interest based on the image stored in the image storage unit 37. Specifically, the CT value calculating unit 38 reads a reconstructed image from the image storage unit 37 whenever the image reconstruction processing unit 36 reconstructs an image. For each read image, the CT value calculating unit 38 calculates the CT value of the region of interest set in advance and successively notifies the system controlling unit 39 of the CT value. The region of interest of which the CT value is calculated can be set manually by the operator in advance. Alternatively, the region of interest can be set by an area of the heart being automatically detected from the reconstructed image.

The system controlling unit 39 controls operations performed by the gantry device 10, the patient couch device 20, and the console device 30, thereby controlling the overall X-ray CT apparatus. For example, when an electrocardiographic synchronized imaging operation is performed, the system controlling unit 39 controls the scan controlling unit 33 and collects the projection data based on instructions from the operator entered using the input device 31 and the electrocardiographic signal outputted from the electrocardiograph 17. The system controlling unit 39 controls the image reconstruction processing unit 36 and reconstructs the image from the projection data based on the notification sent from the CT value calculating unit 38.

Specifically, when the contrast medium is injected into the subject P and an instruction to start imaging is received from the operator, the system controlling unit 39 first controls the scan controlling unit 33 and moves the top plate 22 until the subject P's heart reaches a scanning position. When the top plate 22 moves to the scanning position, the system controlling unit 39 detects the cardiac cycle based on an R wave frequency of the electrocardiographic signal outputted from the electrocardiograph 17. The system controlling unit 39 controls the scan controlling unit 33, and irradiates the subject P's heart with the X-rays of the specific phase range at each detected cardiac cycle. The system controlling unit 39 then collects the projection data.

At this time, the system controlling unit 39 specifies the imaging conditions to the scan controlling unit 33. The imaging conditions include tube voltage and tube current supplied to the X-ray tube 12 from the high voltage generating unit 11, the X-ray exposure timing, the X-ray exposure duration, and the like. Here, it is assumed that the tube voltage and tube current, and the X-ray exposure duration are set in advance by the operator. Also, it is assumed that the X-ray exposure timing is automatically set based on the cardiac cycle, and a phase range set in advance by the operator.

In addition to collecting the projection data, the system controlling unit 39 inputs the CT value of which notification is successively given by the CT value calculating unit 38. The system controlling unit 39 reconstructs the image from the projection data by controlling the image reconstruction processing unit 36 based on changes with time in the inputted CT value.

At this time, the system controlling unit 39 specifies reconstruction conditions to the image reconstruction processing unit 36. The reconstruction conditions include the reconstruction mode used when the image is reconstructed from the projection data. When specifying the reconstruction conditions, the system controlling unit 39 judges whether the CT value inputted from the CT value calculating unit 38 exceeds a predetermined threshold value. When the CT value exceeds the threshold value, the system controlling unit 39 sets segment reconstruction as the reconstruction mode in the reconstruction conditions specified to the image reconstruction processing unit 36. On the other hand, when the inputted CT value does not exceed a predetermined threshold value, the system controlling unit 39 sets half reconstruction as the reconstruction mode in the reconstruction conditions specified to the image reconstruction processing unit 36.

As a result, when the CT value calculated by the CT value calculating unit 38 does not exceed a predetermined threshold value, the reconstruction mode used when the image is reconstructed from the projection data is half reconstruction. On the other hand, when the CT value exceeds a predetermined threshold value, the reconstruction mode is the segment reconstruction. The predetermined threshold value is set in advance by the operator based on an absolute CT value, a relative CT value, or a rate of change of the CT value.

When an instruction to complete imaging is received from the operator, the system controlling unit 39 stops irradiating the X-rays and rotating the rotation frame 15 by controlling the scan controlling unit 33. The system controlling unit 39 also moves the top plate 22 to a predetermined position outside of the gantry device 10.

Figure 3:
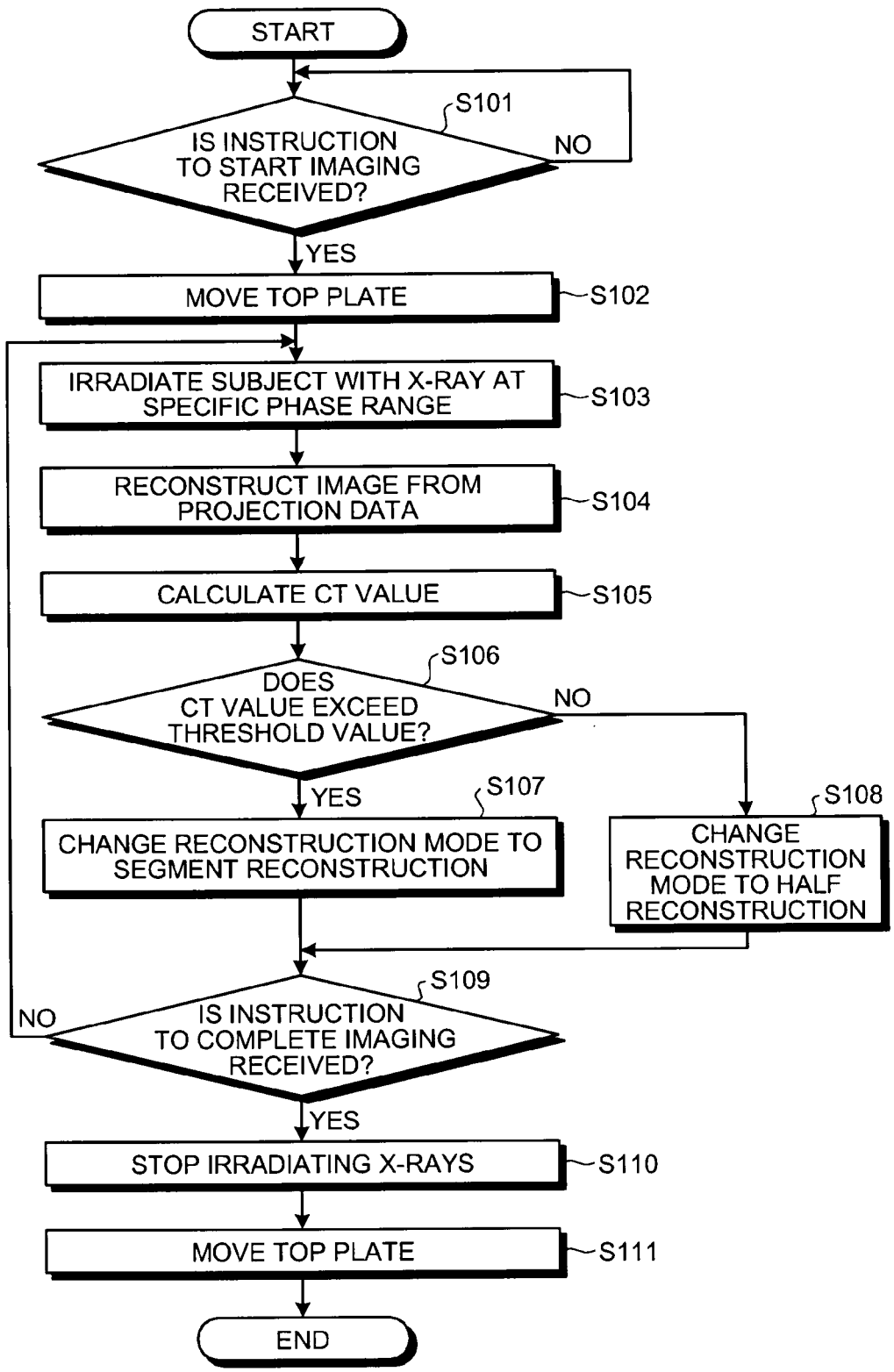
FIG. 3 is a flowchart of processes performed by the X-ray CT apparatus according to the first embodiment.

Next, processes performed by the X-ray CT apparatus according to the first embodiment will be described. FIG. 3 is a flowchart of the processes performed by the X-ray CT apparatus according to the first embodiment. As shown in FIG. 3, in the X-ray CT apparatus, when the console device 30 receives the instruction from the operator to start imaging (Yes at Step S101), the patient couch device 20 moves the top plate 22 until the subject P's heart reaches the scan position (Step S102).

Next, the gantry device 10 irradiates the subject P's heart with the X-rays of the specific phase range at each cardiac cycle (Step S103). The console device 30 reconstructs the image from the projection data (Step S104). The console device 30 then calculates the CT value of the region of interest based on the reconstructed image (Step S105).

Then, when the CT value exceeds a predetermined threshold value (Yes at Step S106), the console device 30 changes the reconstruction mode used when the image is reconstructed to segment reconstruction (Step S107). On the other hand, when the CT value does not exceed a predetermined threshold value (No at Step S106), the console device 30 changes the reconstruction mode to half reconstruction (Step S108).

The console device 30 repeats the processes at Steps S103 to S108 (No at Step S109) until the instruction to complete imaging is received from the operator. When the instruction to complete imaging is received from the operator (Yes at Step S109), the console device 30 stops irradiating the X-rays (Step S110). The patient couch device 20 moves the top plate 22 to a predetermined position outside of the gantry device 10 (Step S111).

Here, the instructions to start imaging and complete imaging are given by the operator. However, for example, imaging can automatically start and end based on the CT value.

As described above, according to the first embodiment, the CT value calculating unit 38 calculates the CT value of the region of interest with time. Based on whether the CT value calculated by the CT value calculating unit 38 exceeds a predetermined threshold value, the system controlling unit 39 changes the reconstruction mode between half reconstruction and segment reconstruction to change the temporal resolution. Therefore, when the examinations are collectively performed during the series of electrocardiographic synchronized imaging operations, the projection data required in each examination can be efficiently collected and the required image can be reconstructed while suppressing radiation exposure of the subject.

Specifically, according to the first embodiment, at a timing at which the concentration of the contrast medium is low, the projection data of the specific phase range is collected and the image is reconstructed using half reconstruction. On the other hand, at a timing at which the concentration of the contrast medium is high, the projection data of the specific phase range is collected and the image is reconstructed using segment reconstruction. Therefore, an image suitable for the myocardial perfusion and the CTA can be obtained.

According to the first embodiment, when the reconstruction mode is segment reconstruction while the CT value of the region of interest exceeds a predetermined threshold value and the reconstruction mode is half reconstruction while the CT value of the region of interest does not exceed a predetermined threshold value is described. However, for example, after the reconstruction mode is changed to the segment reconstruction, the reconstruction mode can be returned to half reconstruction when the image is reconstructed from a projection data set of a predetermined number of heartbeats used in segment reconstruction, as described hereinafter according to a second embodiment.

Figure 4:
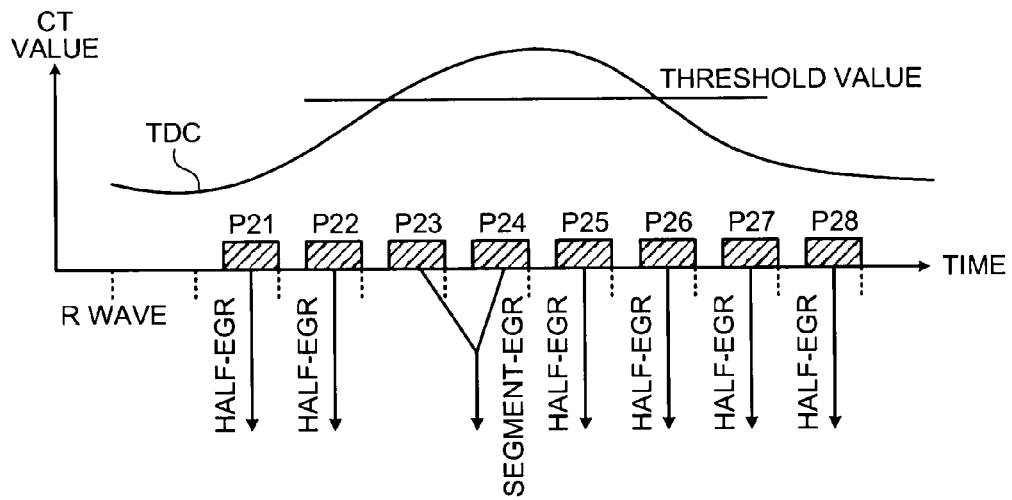
FIG. 4 is an explanatory diagram explaining a concept of electrocardiographic synchronized imaging performed by an X-ray CT apparatus according to a second embodiment.

FIG. 4 is an explanatory diagram explaining a concept of electrocardiographic synchronized imaging performed by an X-ray CT apparatus according to the second embodiment. As shown in FIG. 4, in the X-ray CT apparatus according to the second embodiment, the system controlling unit 39 of the console device 30 judges whether the CT value inputted by the CT value calculating unit 38 exceeds a predetermined threshold value. When the CT value exceeds the threshold value, the system controlling unit 39 specifies the reconstruction conditions to the image reconstruction processing unit 36 in which the reconstruction mode is segment reconstruction. In addition, the system controlling unit 39 instructs the image reconstruction processing unit 36 to return the reconstruction mode to half reconstruction when the image is reconstructed from the projection data set of a predetermined number of heartbeats used in segment reconstruction (a projection data set collected at "P23" and "P24" in FIG. 4). The number of heartbeats used when the image is reconstructed using segment reconstruction (two heartbeats in the example in FIG. 4) is set in advance by the operator.

In this way, according to the second embodiment, after the CT value of the region of interest exceeds a predetermined threshold value, the system controlling unit 39 sets the reconstruction mode to segment reconstruction for only the projection data set of the number of heartbeats used in segment reconstruction. Therefore, a duration of segment reconstruction can be minimized. It is generally known that, because segment reconstruction requires the projection data of a plurality of heartbeats, a longer amount of time is required to obtain the image compared to half reconstruction. Therefore, for example, in the case where the scanning can be stopped at a time when the projection data for reconstructing the segments are collected, if the duration of segment reconstruction is minimized, an overall duration of an imaging operation can be shortened. As a result, an amount of radiation exposure of the subject P can be suppressed.

According to the first embodiment, when the X-ray exposure duration included in the imaging conditions is set in advance by the operator is described. However, the X-ray exposure duration can be extended to a predetermined length when the CT value exceeds a predetermined threshold value, as described hereinafter according to a third embodiment.

Figure 5:
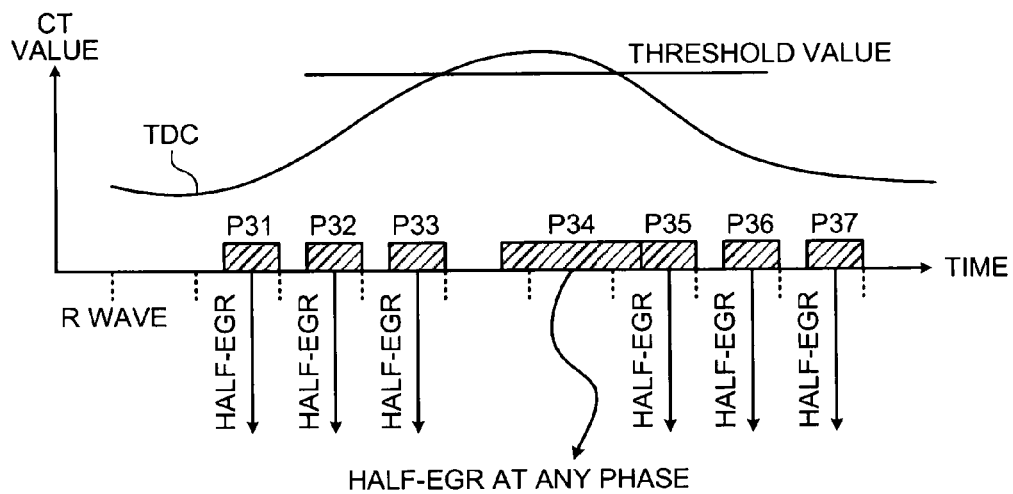
FIG. 5 is an explanatory diagram explaining a concept of electrocardiographic synchronized imaging performed by an X-ray CT apparatus according to a third embodiment.

FIG. 5 is an explanatory diagram explaining a concept of electrocardiographic synchronized imaging performed by an X-ray CT apparatus according to the third embodiment. As shown in FIG. 5, in the X-ray CT apparatus according to the third embodiment, the system controlling unit 39 of the console device 30 judges whether the CT value inputted from the CT value calculating unit 38 exceeds a predetermined threshold value. When the CT value exceeds the threshold value, the system controlling unit 39 specifies the imaging conditions to the scan controlling unit 33 in which the X-ray exposure duration is extended to a predetermined length (see "P34" in FIG. 5).

Here, it is assumed that a predetermined length to which to extend the X-ray exposure duration is set in advance by the operator. For example, when a range from a certain R wave to a next R wave is defined as 0% to 100% as a unit indicating a width of the phase range, although the width of the phase range is ordinarily 65% to 85%, the system controlling unit 39 changes the imaging conditions such that the width of the phase range is 0% to 99% or 50% to 100%.

As a result, for example, when the X-ray exposure duration of the X-rays irradiated at a timing "P34" is extended to a length including all phases of the cardiac cycle, as shown in FIG. 5, the pieces of projection data collected through X-ray exposure over the duration includes those of all phases of the cardiac cycle. Therefore, images of any phase can be reconstructed. FIG. 5 shows when an image is reconstructed from the projection data collected at the timing "P34" using half reconstruction.

In this way, according to the third embodiment, when the CT value of the region of interest exceeds a predetermined threshold value, the system controlling unit 39 specifies the imaging conditions in which the X-ray exposure duration is extended to a predetermined length. Therefore, an image suitable for the CFA which requires the projection data of all phase ranges of the cardiac cycle to be collected, in addition to the myocardial perfusion, can be obtained through the series of electrocardiographic synchronized imaging operations.

According to the third embodiment, when the X-ray exposure duration is extended to a predetermined length while the CT value of the region of interest exceeds a predetermined threshold value is described. However, for example, when the CT value exceeds a predetermined threshold value, the X-rays can be continuously irradiated for a predetermined number of heartbeats after the X-ray exposure duration is extended to a predetermined length, as described hereinafter according to a fourth embodiment.

Figure 6:
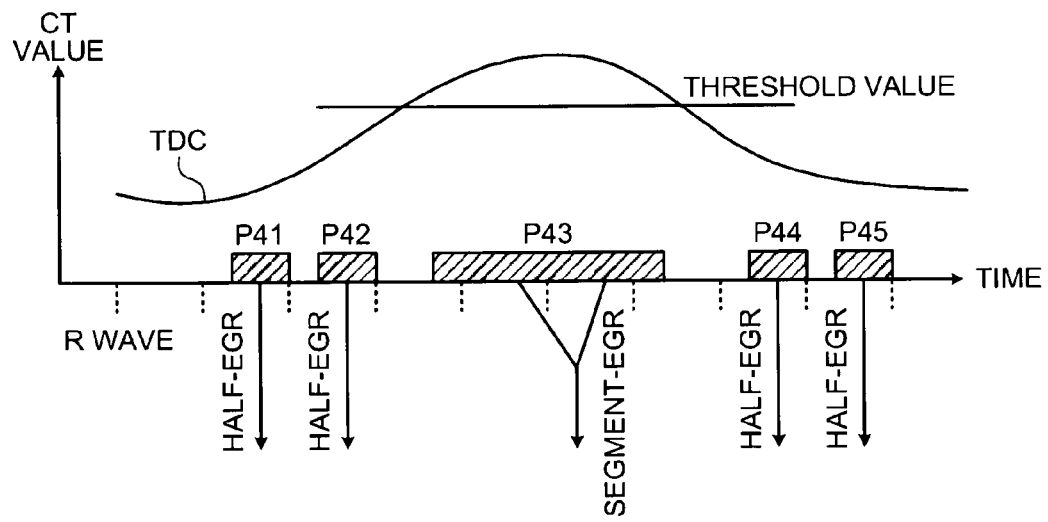
FIG. 6 is an explanatory diagram explaining a concept of electrocardiographic synchronized imaging performed by an X-ray CT apparatus according to a fourth embodiment.

FIG. 6 is an explanatory diagram explaining a concept of electrocardiographic synchronized imaging performed by the X-ray CT apparatus according to the fourth embodiment. As shown in FIG. 6, in the X-ray CT apparatus according to the fourth embodiment, the system controlling unit 39 of the console device 30 judges whether the CT value inputted by the CT value calculating unit 38 exceeds a predetermined threshold value. When the CT value exceeds a predetermined threshold value, the system controlling unit 39 specifies imaging conditions to the scan controlling unit 33 in which the X-ray exposure duration is extended to a predetermined length for a predetermined number of heartbeats (two heartbeats in the example in FIG. 6) (see "P43" in FIG. 6).

As a result, for example, when the X-rays are continuously irradiated for a predetermined number of heartbeats used in segment reconstruction after the X-ray exposure duration of the X-rays irradiated at a timing "P43" is extended to a length including all phases of the cardiac cycle, the pieces of projection data collected through the X-ray exposure over the duration includes those of all phases of the cardiac cycle. Therefore, the images of any phase can be reconstructed. Moreover, segment reconstruction can be performed using the pieces of projection data collected through the X-ray exposure over the duration.

In this way, according to the fourth embodiment, when the CT value of the region of interest exceeds a predetermined threshold value, the system controlling unit 39 specifies the imaging conditions such that the X-rays are continuously irradiated for a predetermined number of heartbeats after the X-ray exposure duration is extended to a predetermined length. Therefore, an image suitable for the CFA which requires the projection data of all phase ranges of the cardiac cycle to be collected, in addition to the myocardial perfusion and the CTA can be obtained through the series of electrocardiographic synchronized imaging operations.

According to the first to fourth embodiments described above, when the tube current applied to the X-ray tube 12 by the high voltage generating unit 11 is set by the operator in advance is described. However, for example, the tube current can be increased to a predetermined value when the CT value of the region of interest exceeds a predetermined threshold value. As a result of the tube current applied by the high voltage generating unit 11 being increased, a dose of X-rays generated by the X-ray tube 12 can be increased. Therefore, an image can be obtained in which an imaging subject is more clearly imaged.

When the tube current is increased while the CT value of the region of interest exceeds a predetermined threshold value is described hereinafter, according to a fifth embodiment. FIG. 7 to FIG. 10 are explanatory diagrams explaining a concept of electrocardiographic synchronized imaging performed by an X-ray CT apparatus according to the fifth embodiment. FIG. 7 to FIG. 10 show when the tube current is increased to a predetermined value while the CT value exceeds a predetermined threshold value in the electrocardiographic synchronized imaging operations described according to the first to fourth embodiments, respectively.

Figure 7:
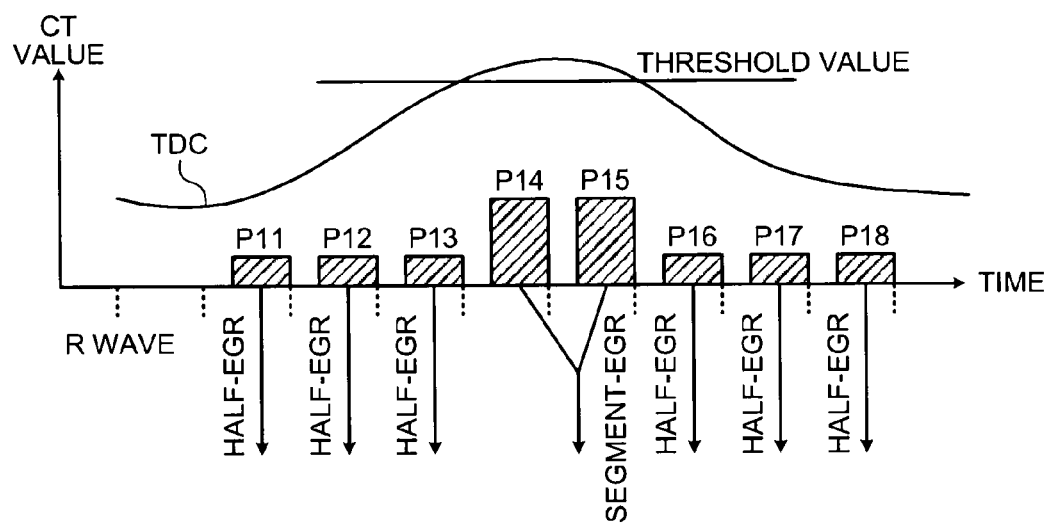
FIG. 7 to FIG. 10 are explanatory diagrams explaining a concept of electrocardiographic synchronized imaging performed by an X-ray CT apparatus according to a fifth embodiment.

As shown in FIG. 7, in the X-ray CT apparatus according to the first embodiment, while the CT value of the region of interest exceeds a predetermined threshold value, the system controlling unit 39 of the console device 30 specifies the reconstruction conditions to the image reconstruction processing unit 36 in which the reconstruction mode is segment reconstruction. The system controlling unit 39 also specifies the imaging conditions to the scan controlling unit 33 such as to increase the tube current to a predetermined value (see "P14" and "P15" in FIG. 7).

As a result, at the timing at which the concentration of the contrast medium is high, strong X-rays are irradiated and the projection data is collected. The image is reconstructed from the collected projection data using half reconstruction. A region of the imaging subject (such as a coronary artery) is more clearly imaged in the image, compared to the image picked up without strengthening the X-rays. Therefore, an image more suitable for the CTA can be obtained.

Figure 8:
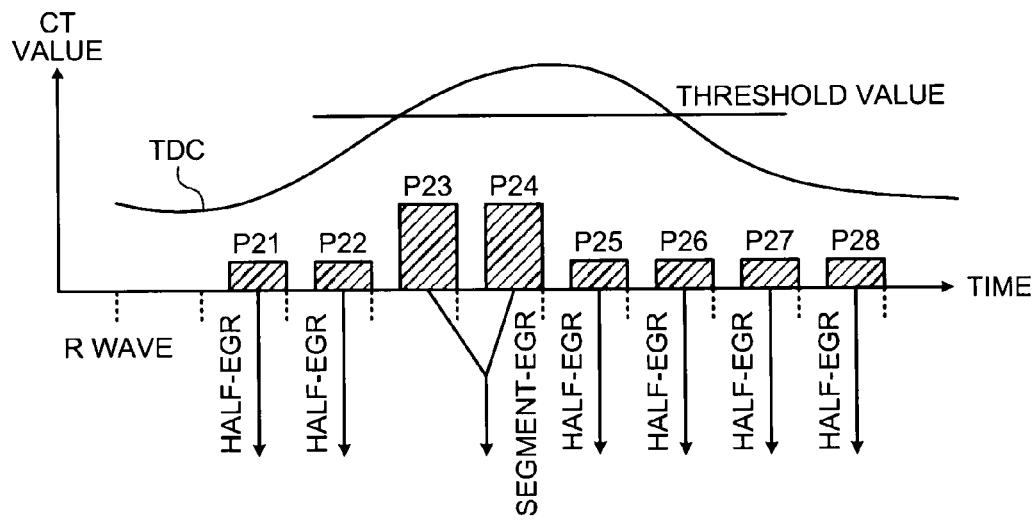

As shown in FIG. 8, in the X-ray CT apparatus according to the second embodiment, when the CT value of the region of interest exceeds a predetermined threshold value, the system controlling unit 39 of the console device 30 specifies the reconstruction conditions to the image reconstruction processing unit 36 in which the reconstruction mode is segment reconstruction. The system controlling unit 39 also instructs the image reconstruction processing unit 36 to return the reconstruction mode to half reconstruction when the image is reconstructed from the projection data set (a projection data set collected to "P23" and "P24" in FIG. 8) of a predetermined number of heartbeats used in segment reconstruction. The system controlling unit 39 specifies the imaging conditions to the scan controlling unit 33 such as to increase the tube current to a predetermined value. The system controlling unit 39 also instructs the scan controlling unit 33 to return the tube current to an original strength when the X-rays are irradiated for a predetermined number of heartbeats (see "P23" and "P24" in FIG. 8).

As a result, the duration of segment reconstruction is minimized and an image can be obtained in which the region of the imaging subject (such as the coronary artery) is more clearly imaged. Therefore, an image more suitable for the CTA can be obtained while suppressing radiation exposure of the subject P.

Figure 9:
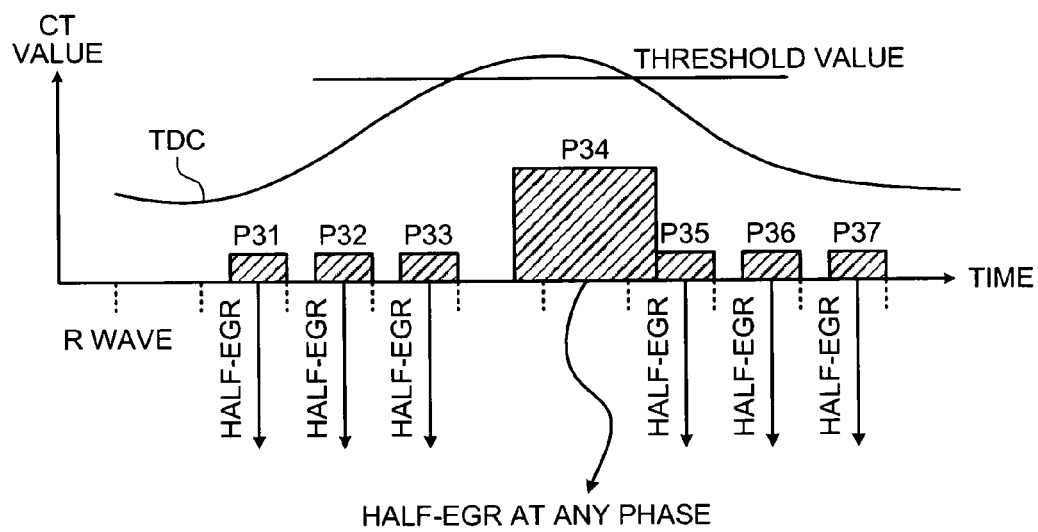

As shown in FIG. 9, in the X-ray CT apparatus according to the third embodiment, when the CT value of the region of interest exceeds a predetermined threshold value, the system controlling unit 39 of the console device 30 specifies the imaging conditions to the scan controlling unit 33 such that the X-ray exposure duration is extended to a predetermined length and the tube current is increased to a predetermined value (see "P34" in FIG. 9).

As a result, in the image reconstructed from the projection data collected over a wide phase range, the region of the imaging subject is more clearly imaged compared to the image picked up without strengthening the X-rays. Therefore, an image more suitable for the CFA can be obtained.

In FIG. 9, the dose of X-rays irradiated at a timing "P35" is shown to be the same as the dose of X-rays irradiated at timings "P31" to "P33" and the like to simplify the description. However, when the X-ray tube 12 is, for example, an X-ray tube adopting a filament, a temperature of the filament in the X-ray tube 12 does not immediately decrease. Therefore, in actuality, the dose of X-rays irradiated at the timing "P35" subsequent to a timing "P34" may be greater than the dose of X-rays irradiated at the timings "P31" to "P33".

Figure 10:
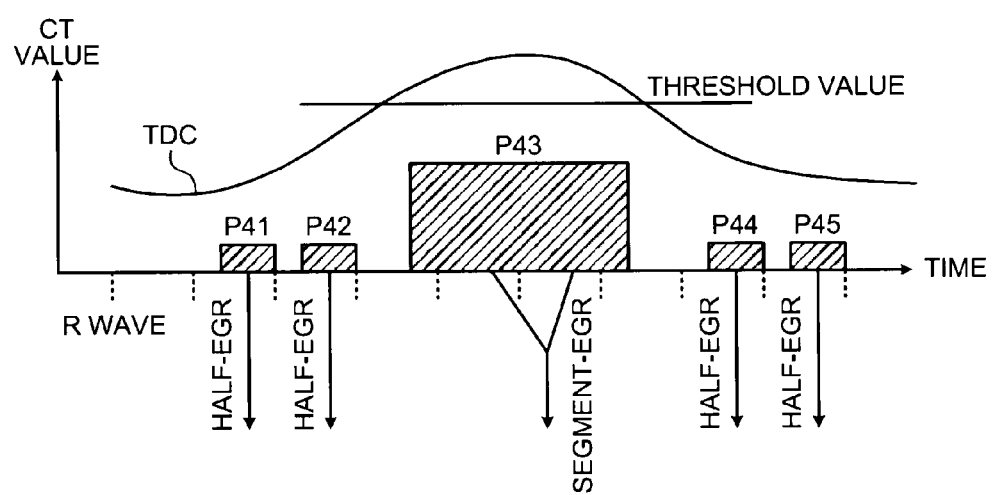

As shown in FIG. 10, in the X-ray CT apparatus according to the fourth embodiment, when the CT value of the region of interest exceeds a predetermined threshold value, the system controlling unit 39 of the console device 30 specifies the imaging conditions to the scan controlling unit 33 such that the X-ray exposure duration is extended to a predetermined length for a predetermined number of heartbeats (two heartbeats in the example in FIG. 10) and the tube current is increased to a predetermined value (see "P43" in FIG. 9).

As a result, in the image reconstructed from the pieces of projection data collected at a plurality of cardiac cycles and over a wide phase range, the region of the imaging subject is more clearly imaged compared to the image picked up without strengthening the X-rays. Therefore, an image more suitable for the CTA and the CFA can be obtained.

As described above, according to the fifth embodiment, at the timing at which the concentration of the contrast medium is high, the dose of the irradiated X-rays increase. The image is reconstructed using segment reconstruction, and the X-ray exposure duration is extended. Therefore, the projection data required in each examination can be more efficiently collected and the required image can be reconstructed.

According to the above-described embodiments, in the X-ray exposure performed at any of "P11" to "P18" in FIG. 1 and FIG. 7, "P21" to "P28" in FIG. 4 to FIG. 8, "P31" to "P37" in FIG. 5 and FIG. 9, and "P41" to "P45" in FIG. 6 and FIG. 10, it is assumed that an X-ray irradiation width in a body axis direction of the subject P is a width allowing an amount of projection data required to obtain an image for examination to be collected.

According to each embodiment, when whether the CT value of the region of interest exceeds a predetermined threshold value is judged, and the reconstruction mode, the X-ray exposure duration, and the X-ray exposure dose are automatically switched based on a judgment result is described. However, the X-ray CT apparatus can include a graphical user interface (GUI) used to change the reconstruction mode, the X-ray exposure duration, and the X-ray exposure dose at the discretion of the operator.

For example, the system controlling unit 39 displays a graphic in the display device 32. The graphic shows the changes with time in the CT value of the region of interest and the X-ray exposure timings, such as the TDC and the "P11" to "P18" in FIG. 1. The system controlling unit 39 also receives operation input regarding the displayed graphic through the input device 31. The input device 31 is a mouse, a keyboard, and the like. Based on the received operation input, the system controlling unit 39 specifies the imaging conditions to the scan controlling unit 33, specifies the reconstruction conditions to the image reconstruction processing unit 36, and changes the reconstruction mode, the X-ray exposure duration, and the X-ray exposure dose.

Figure 11A:
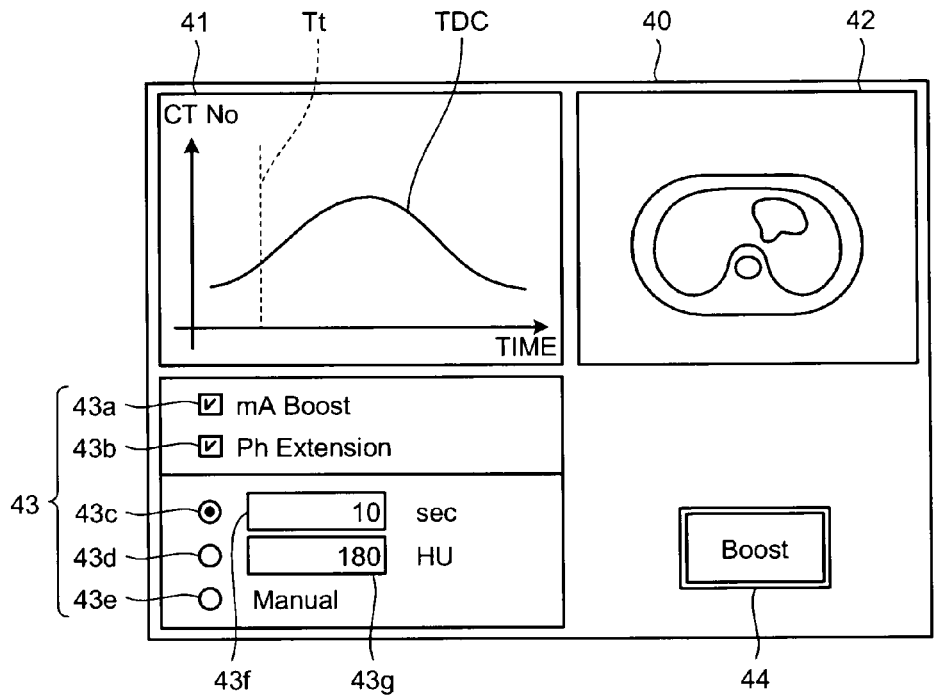
FIG. 11A to FIG. 11C are diagrams illustrating examples of a GUI for inputting an instruction to change imaging conditions related to X-ray exposure.
Figure 11B:
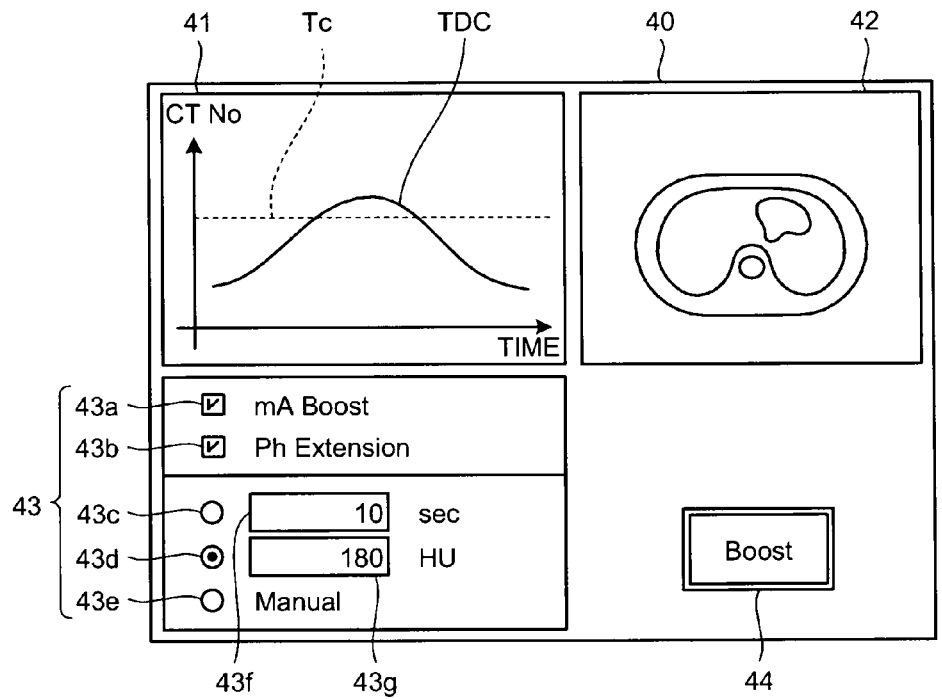
Figure 11C:
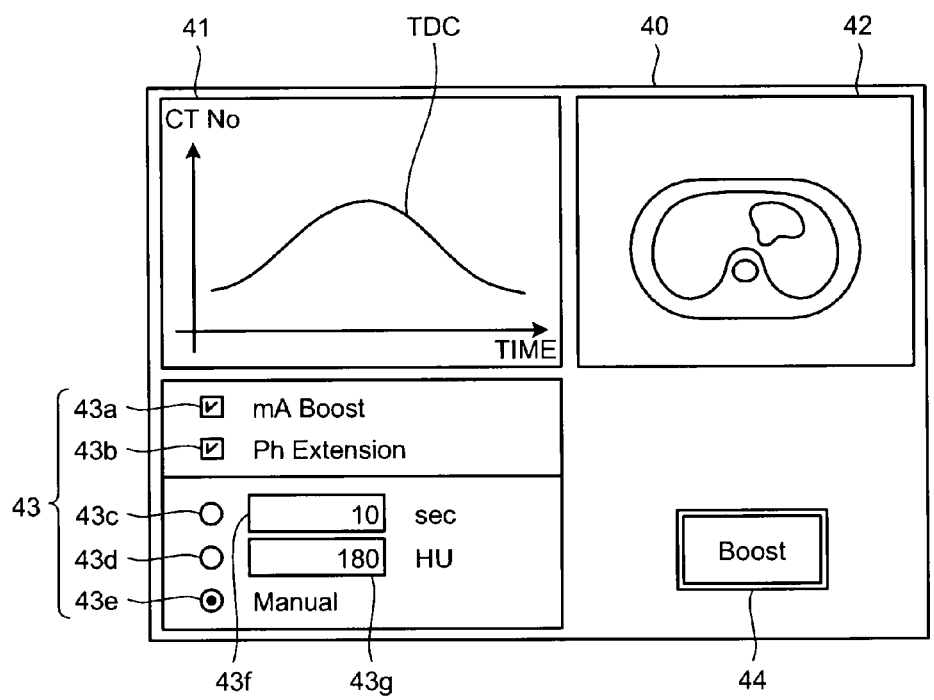

An example of a GUI used to input an instruction to change the imaging conditions related to X-ray exposure will be described. FIG. 11A to FIG. 11C show the example of the GUI used to input the instruction to change the imaging conditions related to X-ray exposure. As showing in FIG. 11A to FIG. 11C, for example, a GUI 40 includes a TDC display area 41, an image display area 42, an information input area 43, and a Boost button 44. The TDC display area 41 displays the TDC. The image display area 42 displays the reconstructed image. The information input area 43 allows the operator to input information related to the change in the imaging conditions. The Boost button 44 allows the operator to instruct that the imaging conditions be changed. In the TDC display area 41, "CT No" indicates the CT value of the region of interest, and "time" indicates an elapsed time from the start of the examination.

The information input area 43 includes check boxes 43a and 43b used to select details of the change in the imaging conditions. A check box 43a is used to select increase in the tube current indicating the X-ray exposure dose (mA Boost). A check box 43b is used to select extension of the phase range indicating the X-ray exposure duration (Ph Extension).

The information input area 43 also includes radio buttons 43c, 43d and 43e used to select whether to change the imaging conditions automatically or manually. A radio button 43c is used to select changing the imaging conditions automatically based on the elapsed time from the start of the examination. A text box 43f is positioned next to the radio button 43c. An elapsed time serving as a threshold value is entered in the text box 43f. The radio button 43d is used to select changing the imaging conditions automatically based on the CT value of the region of interest. A text box 43g is positioned next to the radio button 43d. A CT value serving as a threshold value is entered in the text box 43g. The radio button 43e is used to select changing the imaging conditions manually.

Operations performed by the X-ray CT apparatus when the GUI 40 is used will be described. First, in the X-ray CT apparatus, in response to a request from the operator inputted from the input device 31, the system controlling unit 39 displays the GUI 40 in the display device 32. At this time, the system controlling unit 39 outputs a TDC in the TDC display area 41 based on the CT value of which notification is given by the CT value calculating unit 38. The system controlling unit 39 also reads the image reconstructed by the image reconstruction processing unit 36 from the image storage unit 37 and outputs the reconstructed image in the image display area 42.

Then, for example, it is assumed that the operator checks the check boxes 43a and 43b and further checks the radio button 43c as shown in FIG. 11A. In this case, in the X-ray CT apparatus, the system controlling unit 39 of the console device 30 outputs a straight line Tt in the TDC display area 41. The straight line Tt indicates an amplitude of the threshold value entered in the text box 43f (10 seconds in the example in FIG. 11A). The system controlling unit 39 also measures the elapsed time from the start of the examination and judges whether the measured elapsed time exceeds the threshold value entered in the text box 43f. When the elapsed time exceeds the threshold value, the system controlling unit 39 instructs the scan controlling unit 33 to increase the X-ray exposure dose to a predetermined amount and extend the X-ray exposure duration to a predetermined range (such as a range covering all phases of a single heartbeat). As a result, the imaging conditions are automatically changed based on the elapsed time from the start of the examination.

For example, as shown in FIG. 11B, it is assumed that the operator checks the check boxes 43a and 43b and further checks the radio button 43d. In this case, in the X-ray CT apparatus, the system controlling unit 39 of the console device 30 outputs a straight line Tc in the TDC display area 41. The straight line Tc indicates an amplitude of the threshold value entered in the text box 43g (180 Hounsfield units [HU] in the example in FIG. 11B). The system controlling unit 39 also judges whether the CT value entered by the CT value calculating unit 38 exceeds the threshold value entered in the text box 43g. When the CT value exceeds the threshold value, the system controlling unit 39 instructs the scan controlling unit 33 to increase the X-ray exposure dose to a predetermined amount and extend the X-ray exposure duration to a predetermined range. As a result, the imaging conditions are automatically changed based on the CT value of the region of interest.

For example, as shown in FIG. 11C, it is assumed that the operator checks the check boxes 43a and 43b and further checks the radio button 43e. In this case, in the X-ray CT apparatus, the system controlling unit 39 of the console device 30 instructs the scan controlling unit 33 to increase the X-ray exposure dose to a predetermined amount and extend the X-ray exposure duration to a predetermined range at a timing at which a depressing operation of the Boost button 44 is inputted by the input device 31. As a result, the imaging conditions are changed based on an instruction from the operator.

In each example described above, when the check boxes 43a and 43b are respectively checked is described. However, when only the check box 43a is checked, only the X-ray exposure dose is increased to a predetermined amount. When only the check box 43b is checked, only the X-ray exposure duration is extended to a predetermined range.

In this way, in the X-ray CT apparatus, the system controlling unit 39 changes the reconstructing conditions based on the changes with time in the CT value of the region of interest. The system controlling unit 39 also displays the TDC indicating the changes with time in the CT value and the GUI 40 used to input instructions to change the imaging conditions related to X-ray exposure. The input device 31 inputs the instruction to change the imaging conditions through the GUI 40. When the instruction to change the imaging conditions is inputted, the system controlling unit 39 changes the imaging conditions related to X-ray exposure. As a result, the imaging conditions can be changed at an arbitrary timing while viewing the TDC. The phase range and the temporal resolution of the imaging data can be more flexibly adjusted according to the examination type.

According to each embodiment, the descriptions are given under an assumption that two or more examinations, among the myocardial perfusion, the CTA, and the CFA, are collectively performed in the series of electrocardiographic synchronized imaging operations. However, the present invention is not limited thereto. The invention can be similarly applied when other types of examinations are performed.

Additional advantages and modifications will readily occur to those skilled in the art. Therefore, the invention in its broader aspects is not limited to the specific details and representative embodiments shown and described herein. Accordingly, various modifications may be made without departing from the spirit or scope of the general inventive concept as defined by the appended claims and their equivalents.

What is claimed is:

1. An X-ray CT apparatus comprising:
an electrocardiographic information collecting unit that collects electrocardiographic information;
a data collecting unit that collects multidirectional projection data obtained by irradiating a subject with X-rays;
an image reconstructing unit that reconstructs a CT image in approximately real time based on the electrocardiographic information collected by the electrocardiographic information collecting unit and the multidirectional projection data collected by the data collecting unit;
a concentration calculating unit that calculates, in approximately real time, a CT value of the reconstructed CT image with time within a region of interest, the CT value serving as an indicator of a concentration of a contrast medium; and
a reconstruction mode changing unit that changes, in approximately real time, a reconstruction mode of reconstructing the CT image from the multidirectional projection data, during a scan for obtaining an image for examination, based on the concentration calculated by the concentration calculating unit.

2. The apparatus according to claim 1, further comprising:
an imaging condition changing unit that changes imaging conditions related to irradiation of the X-rays based on the concentration calculated by the concentration calculating unit.

3. The apparatus according to claim 1, wherein the reconstruction mode changing unit changes the reconstruction mode to change a temporal resolution of an image to be reconstructed based on the concentration calculated by the concentration calculating unit.

4. The apparatus according to claim 2, wherein the imaging condition changing unit changes the imaging conditions in which an exposure duration of the X-rays is extended to a predetermined length when the concentration calculated by the concentration calculating unit exceeds a predetermined threshold value.

5. The apparatus according to claim 2, wherein the imaging condition changing unit changes the imaging conditions such as to increase an exposure dose of the X-rays to a predetermined value while the concentration calculated by the concentration calculating unit exceeds a predetermined threshold value.

6. The apparatus according to claim 2, wherein,
the reconstruction mode changing unit changes the reconstruction mode based on whether the concentration exceeds a predetermined threshold value, and
the imaging condition changing unit changes the imaging conditions based on whether the concentration exceeds a predetermined threshold value.

7. The apparatus according to claim 6, wherein the predetermined threshold value is a threshold value defined based on an absolute CT value, a relative CT value, or a rate of change of the CT value.

8. The apparatus according to claim 2, further comprising:
a condition information display unit that respectively displays information indicating change in the concentration with time calculated by the concentration calculating unit, information indicating the reconstruction mode, and information indicating the imaging conditions; and
a condition changing-instruction input unit that receives an instruction for changing in each of information displayed by the condition information display unit, wherein,
the reconstruction mode changing unit changes the reconstruction mode based on the instruction received by the condition changing-instruction input unit, and
the imaging condition changing unit changes the imaging conditions based on the instruction received by the condition changing-instruction input unit.

9. An X-ray CT apparatus comprising:
an electrocardiographic information collecting unit that collects electrocardiographic information;
a data collecting unit that collects multidirectional projection data obtained by irradiating a subject with X-rays;
an image reconstructing unit that reconstructs a CT image based on the electrocardiographic information collected by the electrocardiographic information collecting unit and the multidirectional projection data collected by the data collecting unit;
a concentration calculating unit that calculates a concentration of a contrast medium with time within a region of interest in approximately real time; and
an X-ray controlling unit that irradiates a subject with X-rays synchronously with the electrocardiographic information when the concentration calculated by the concentration calculating unit exceeds a predetermined threshold value, and controls irradiation of a subject with X-rays asynchronously with the electrocardiographic information when the concentration calculated by the concentration calculating unit does not exceed a predetermined threshold value.

10. The apparatus according to claim 1, wherein the reconstruction mode changing unit switches between a first reconstruction mode in which the CT image is reconstructed from projection data of a plurality of heartbeats and a second reconstruction mode in which the CT image is reconstructed from projection data of one heartbeat.

11. An X-ray CT apparatus comprising:
an electrocardiographic information collecting unit that collects electrocardiographic information;
a data collecting unit that collects multidirectional projection data obtained by irradiating a subject with X-rays;
an image reconstructing unit that reconstructs a CT image in approximately real time based on the electrocardiographic information collected by the electrocardiographic information collecting unit and the multidirectional projection data collected by the data collecting unit;
a concentration calculating unit that chronologically calculates, in approximately real time, a CT value of the reconstructed CT image with time within a region of interest, the CT value serving as an indicator of a concentration of a contrast medium;

a reconstruction mode changing unit that changes, in approximately real time, a reconstruction mode of reconstructing the CT image from the multidirectional projection data, during a scan for obtaining an image for examination, based on the concentration calculated by the concentration calculating unit;

a display unit that displays information indicating changes in the concentration of the contrast medium with time calculated by the concentration calculating unit and an interface for receiving an instruction to change imaging conditions related to irradiation of the X-rays;

a changing instruction input unit that receives an instruction to change imaging conditions through the interface displayed by the display unit; and an imaging condition changing unit that changes the imaging conditions related to irradiation of the X-rays when the instruction to change the imaging conditions is received by the changing instruction input unit.

* * * * *